United States Patent [19]

Imaki et al.

[11] Patent Number: 4,499,306
[45] Date of Patent: Feb. 12, 1985

[54] 2,2-DIHALO-6-HALO-6-(1-HALOISOBUTYL)-CYCLOHEXANONE

[75] Inventors: Naoshi Imaki, Atsugi; Takemi Nakanome, Sagamihara, both of Japan

[73] Assignee: Mitsubishi Chemical Industries Ltd., Tokyo, Japan

[21] Appl. No.: 475,946

[22] Filed: Mar. 16, 1983

[30] Foreign Application Priority Data

Apr. 7, 1982 [JP] Japan .................................. 57-57546

[51] Int. Cl.³ .............................................. C07C 45/63
[52] U.S. Cl. .................................... 568/348; 568/376; 568/345; 549/469
[58] Field of Search ........................ 568/376, 348, 345

[56] References Cited

U.S. PATENT DOCUMENTS 3,988,369 10/1976 Pearson ................................ 568/376
4,005,147 1/1977 Fischer et al. ...................... 568/345
4,250,341 2/1981 Needham et al. ................... 568/376

Primary Examiner—James H. Reamer
Attorney, Agent, or Firm—Oblon, Fisher, Spivak, McClelland & Maier

[57] ABSTRACT

A 2,2-dihalo-6-halo-6-(1-haloisobutyl)cyclohexanone represented by the general formula

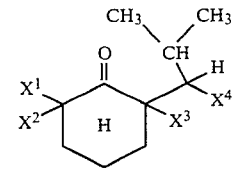

where each of $X^1$, $X^2$, $X^3$ and $X^4$ is a halogen atom.

5 Claims, No Drawings

2,2-DIHALO-6-HALO-6-(1-HALOISOBUTYL)CYCLOHEXANONE

The present invention relates to a 2,2-dihalo-6-halo-6-(1-haloisobutyl)cyclohexanone (hereinafter sometimes referred to simply as "a halogen-substituted isobutylcyclohexanone"). More particularly, the present invention relates to a halogen-substituted isobutylcyclohexanone as a novel intermediate useful for the preparation of known 2,3-dihydro-2,2-dimethyl-7-hydroxybenzofuran (hereinafter referred to simply as "BFL").

BFL is an important compound as an intermediate material for 2,3-dihydro-2,2-dimethylbenzo-7-furanylmethylcarbamate which is a pesticide having a wide pesticidal spectrum and known by the name of Carbofuran. Various processes have been proposed for the preparation of BFL. As typical processes which are practically in use, there may be mentioned those wherein catechol is used as the starting material or o-nitrophenol is used as the starting material.

For instance, Japanese Examined Patent Publication No. 12263/1967 (U.S. Pat. No. 3,474,170 and No. 3,474,171) discloses a process for preparing BFL which comprises reacting catechol with a methallyl halide to form 2-methallyloxyphenol, followed by rearrangement and cyclization.

On the other hand, Japanese Examined Patent Publication No. 9546/1968 (U.S. Pat. No. 3,320,286 and No. 3,412,110) discloses a process for preparaing BFL wherein o-nitrophenol and a methallyl halide are reacted to form 1-methallyloxy-2-nitrobenzene which is then subjected to rearrangement and cyclization to form 2,3-dihyro-2,2-dimethyl-7-nitrobenzofuran which in turn subjected to reduction and diazotization and the resulting diazonium salt is hydrolyzed to obtain BFL.

However, these processes require expensive starting materials and yet do not give good yield. A completely satisfactory process has not yet been developed.

Under these circumstances, the present inventors have conducted extensive researchers to develop a practical process for the preparation of BFL and have succeeded in developing a novel process wherein cyclohexanone and isobutylaldehyde are used as starting materials and a halogen-substituted isobutylcyclohexanone is formed as an intermediate for the process.

The present invention provides a 2,2-dihalo-6-halo-6-(1-haloisobutyl)cyclohexanone represented by the general formula

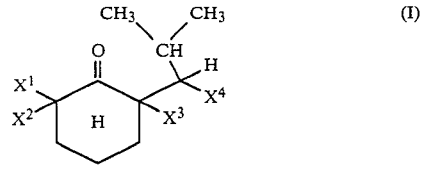

where each of $X^1$, $X^2$, $X^3$ and $X^4$ is a halogen atom, a process for its preparation and a process for the preparation of BFL wherein the compound of the general formula I is used as a starting material.

Now, present invention will be described in detail with reference to the preferred embodiments.

The halogen-substituted isobutylcyclohexanone of the general formula I according to the present invention is a novel intermediate for the preparation of BFL.

In the general formula I, each of $X^1$, $X^2$, $X^3$ and $X^4$ is a halogen atom such as chlorine, bromine or iodine. $X^1$, $X^2$, $X^3$ and $X^4$ may be the same or different halogen atoms. However, in view of the reactivity and economy, chlorine is preferred among them.

As specific examples of the compound of the general formula I, there may be mentioned 2,2-dichloro-6-chloro-6-(1-chloroisobutyl)cyclohexanone, 2,2-dibromo-6-bromo-6-(1-bromoisobutyl)cyclohexanone, 2,2-diiodo-6-iodo-6-(1-iodoisobutyl)cyclohexanone, 2,2-dichloro-6-bromo-6-(1-bromoisobutyl)cyclohexanone, 2,2-dichloro-6-chloro-6-(1-bromoisobutyl)cyclohexanone and 2,2-dichloro-6-chloro-6-(1-iodoisobutyl)cyclohexanone.

The halogen-substituted isobutylcyclohexanone of the present invention may be produced from, for instance, cyclohexanone as a starting material by the following synthesis.

Synthesis 1

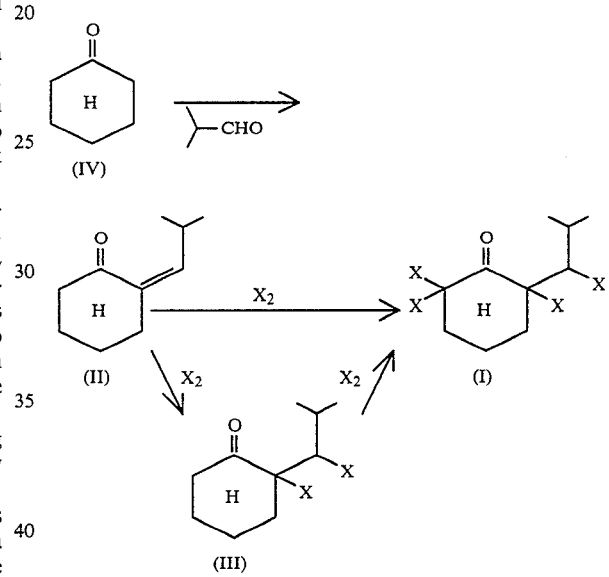

where X is a halogen atom.

2-Isobutylidenecyclohexanone of the formula II may be prepared by cross aldol condensation of cyclohexanone with isobutyl aldehyde (Chemical Abstracts 57, 16424a).

The compound of the formula I is obtained by the reaction of the compound of the formula II with a halogen. This reaction is a combination of two reactions i.e. an addition reaction of the halogen to the double bond and a substitution reaction of the halogen at the α-position of the ketone. These two reactions may be conducted simultaneously or separately. The halogen may be chlorine, bromine or iodine. However, chlorine is preferred.

In the case where the addition reaction and the substitution reaction of the halogen are simultaneously carried out, the stoichiometric amount of the halogen, i.e. three mols per mol of the compound of the formula II, is needed. However, it is practically preferred to use the halogen in an amount within a range of from 3 to 6 mols per mol of the compound of the formula II.

This reaction proceeds in the absence of any catalysts. However, it is preferred to use a catalyst to effectively carry out the reaction. As such a catalyst, there may be used a tertiary amine such as pyridine, collidine, quinoline or methylpyridine, or an organic phosphine or organic phosphine oxide such as triphenyl phosphine, tributyl phosphine or triphenyl phosphine oxide. The amount of the catalyst is usually from 1/100 to ½ mol per mol of the compound of the formula II.

For the halogenation reaction, a solvent is not necessarily required. However, when a solvent is used, the solvent is preferably inert to the halogenation reaction. As such an inert solvent, there may be mentioned a halogen-type solvent such as tetrachlorocyclohexanone, carbon tetrachloride or hexachloroacetone. However, it is advantageous to use the reaction product i.e. the halogen-substituted isobutylcyclohexanone as the solvent. The halogenation reaction is usually conducted at a temperature of from 0° to 150° C., preferably from 50° to 120° C. The reaction may be stopped immediately after the introduction of the halogen. However, in order to complete the reaction, it is preferred to continue the reaction for five hours as the highest limit, preferably for 1 hour, after the completion of the introduction of the halogen.

In the case where the substitution reaction of the halogen at the α-position of the ketone and the addition reaction of the halogen to the double bond are carried out separately, firstly an equimolar amount of the halogen is reacted with the compound of the formula II under a mild condition to add the halogen to the double bond and then from 2 to 3 mols of the halogen per mol of the compound of the formula II is reacted in the presence of a catalyst to substitute the halogen at the α-position of the ketone. The conditions such as the catalyst, the solvent, the reaction temperature and the reaction time may be selected in the same manner as in the case where the addition reaction and the substitution reaction of the halogen are simultaneously carried out.

According to this method, it is possible to differentiate the halogen to be added to the double bond from the halogen to be substituted at the α-position of the ketone. For instance, chlorine is firstly added to the double bond and then bromine is substituted at the α-position of the ketone, whereby 2,2-dibromo-6-chloro-6-(1-chloroisobutyl)cyclohexanone is obtained.

After the reaction, the desired halogen-substituted isobutylcyclohexanone may readily be obtained by washing the reaction solution with water and distilling it under reduced pressure. In the above-mentioned reaction between 2-isobutylidene cyclohexanone and the halogen, a 2,2-dihalo-6-halo-6-(1-haloisobutyl)cyclohexanone forms as the main reaction product but at the same time a small amount of an isomer, forms as a by-product. When reacted in the same manner as the main reaction product i.e. 2,2-dihalo-6-halo-6-(1-haloisobutyl)cyclohexanone, this isomer will give 2,2-dimethyl-2,3-dihydro-7-hydroxybenzofuran. Therefore, it is unnecessary to separate them for the production of BFL. This isomer is assumed to be 2,2-dihalo-6-halo-6-(2-haloisobutyl)cyclohexanone and believed to be formed by the steps of: an addition of the halogen to the double bond→formation of an isobutenyl group by dehydrohalogenation→an addition of a hydrogen halide to the double bond.

2,2-dihalo-6-halo-6-(1-haloisobutyl)cyclohexanone of the formula I thus obtained can be led to BFL which is useful as a starting material for Carbofuran i.e. a carbamate-type agricultural chemical.

BFL is prepared from the halogen-substituted isobutylcyclohexanone of the present invention as the starting material e.g. by the Routes shown in Synthesis 2.

Synthesis 2

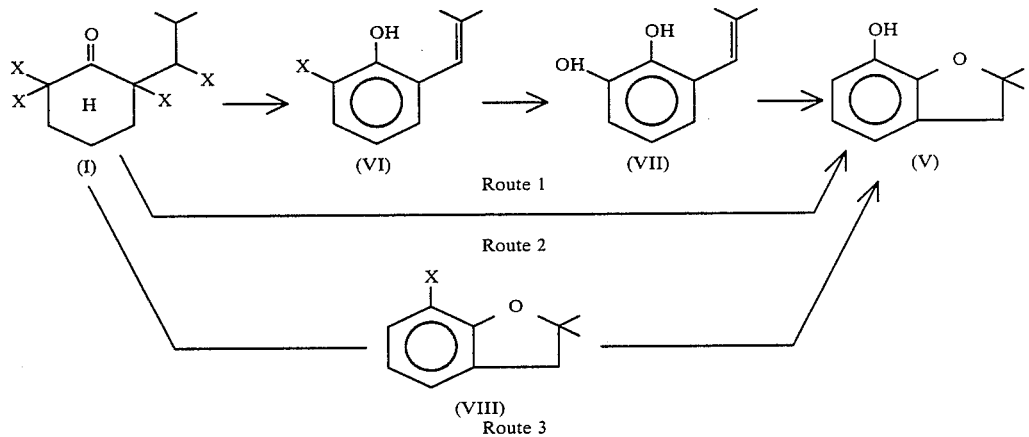

The respective preparation routes will be described in detail.

Route 1: BFL is prepared by (i) a dehydrohalogenation reaction of the halogen-substituted isobutylcyclohexanone, (ii) a hydrolytic reaction and (iii) a cyclization reaction.

(i) Dehydrohalogenation reaction

The halogen-substituted isobutylcyclohexanone of the formula I is heated in the presence of a dehydrohalogenation agent for dehydrohalogenation and aromatic ring formation to form a 2-isobutenyl-6-halophenol of the formula VI.

As the dehydrohalogenation agent, a tertiary amine such as pyridine, picoline, collidine, quinoline, triethylamine or dimethylaniline, or an amide such as dimethylformamide, N-methyl acetanilide, N,N-dimethyl benzoic acid amide may be used. Preferably, a heterocyclic tertiary amine such as pyridine or quinoline or an amide such as dimethylformamide is used. Such a dehydrohalogenation agent is usually used in an amount of from 0.01 to 100 mols, preferably from 1.0 to 50 mols, per mol of the halogen-substituted isobutylcyclohexanone as the starting material. If the amount of the dehydrohalogenation agent is too small, 2,2-dimethyl-2,3-dihydro-7-halobenzofuran of the formula VIII will be formed as a by-product, such being undesirable.

This reaction can be conducted by adding a carboxylic acid salt or a combination of a carboxylic acid and a carboxylic acid salt to the reaction system. As such a carboxylic acid salt, there may be mentioned sodium acetate, potassium acetate, lithium acetate, sodium formate or sodium benzoic acid. As a carboxylic acid, there may be mentioned acetic acid, formic acid or benzoic acid. Such an additive is particularly effective when an amide is used as the dehydrohalogenation agent and it serves to suppress the formation of 2,2-dimethyl-2,3-dihydro-7-halobenzofuran of the formula VII as the by-product. The additive is usually used in an amount of from 0.01 to 100 mols, preferably 0.1 to 10 mols, per mol of the dehydrohalogenation agent.

The reaction temperature is usually from 50° to 250° C., preferably from 100° to 150° C. The reaction time is usually from 0.1 to 10 hours. The dehydrohalogenation agent serves as a reaction solvent, and accordingly no additional solvent is required.

After the completion of the reaction, the 2-isobutenyl-6-halophenol of the formula VI is obtained from the reaction solution by a usual separation and purification means such as extraction or distillation.

(ii) Hydrolytic reaction

The 2-isobutenyl-6-halophenol of the formula VI is hydrolyzed in the presence of a copper compound catalyst and an alkali to form 1,2-dihydroxy-3-isobutenylbenzene.

As the copper compound catalyst, cuprous chloride, cuprous oxide, cupric chloride dihydrate, etc. may be used. Preferred is cuprous chloride. The catalyst is usually used in an amount of from 0.0001 to 10 mols, preferably from 0.01 to 0.3 mol, per mol of the 2-isobutenyl-6-halophenol of the formula VI.

As the alkali, there may be mentioned sodium hydroxide, potassium hydroxide, calcium hydroxide, barium hydroxide octahydrate and the like. Particularly preferred is sodium hydroxide.

As the solvent, water is conveniently used in an amount of from 5 to 100 parts by weight relative to the 2-isobutenyl-6-halophenol.

The reaction temperature is usually from 150° to 250° C., preferably from 170° to 200° C., and the reaction time is usually from 0.1 to 10 hours.

After the completion of the reaction, 1,2-dihydroxy-3-isobutenylbenzene of the formula VII may be obtained by a usual separation and purification means such as extraction and distillation after neutralizing the reaction solution with hydrochloric acid.

(iii) Cyclization reaction

The 1,2-dihydroxy-3-isobutenylbenzene of the formula VII is cyclized in the presence of a catalyst to obtain BFL.

As the catalyst, there may be mentioned a sulfonic acid such as paratoluene sulfonic acid or benzene sulfonic acid, an aluminum compound such as aluminum isopropoxide, an inorganic acid such as sulfuric acid, hydrochloric acid, hydrobromic acid or phosphoric acid, an organic acid such as formic acid, trifluoroacetic acid or trichloroacetic acid, or a metal salt such as magnesium oxide or iron chloride. The catalyst is used usually in an amount of from 0.001 to 10 mols, preferably from 0.01 to 0.1 mols, per mol of the 1,2-dihydroxy-3-isobutenylbenzene.

For the cyclization reaction, a solvent is not necessarily required. However, when a solvent is used, it is preferably inert to the cyclization reaction. As such an inert solvent, there may be mentioned xylene, toluene, water, acetic acid or methyl cellusolve. The amount of the solvent is preferably from 0.1 to 100 ml per gram of the 1,2-dihydroxy-3-isobutenylbenzene.

The heating temperature is usually from 50° to 200° C., preferably from 80° to 150° C., and the reaction time is usually from 0.1 to 20 hours.

After the completion of the reaction, BFL (V) can be obtained from the reaction solution by a usual separation and purification means such as extraction, distillation, etc.

Route 2: The halogen-substituted isobutylcyclohexanone is heated in a carboxylic acid solvent in the presence of a carboxylic acid salt to effect dehydrohalogenation, hydrolysis and cyclization, whereby BFL is prepared.

As the carboxylic acid for the solvent, an optional carboxylic acid such as formic acid, acetic acid, propionic acid, butyric acid, isobutyric acid or valeric acid may be used. A lower aliphatic carboxylic acid having from 1 to 4 carbon atoms are preferred. Particularly preferred is acetic acid.

As the carboxylic acid salt, a metal salt of the above-mentioned carboxylic acid, particularly an alkali metal salt or an alkaline earth metal salt, is used. An alkali metal salt of a lower aliphatic carboxylic acid having from 1 to 4 carbon atoms is preferred. Particularly preferred is an alkali metal salt of acetic acid. The carboxylic acid salt is usually used in an amount of from 2 to 10 mols, preferably from 3 to 5 mols, as the carboxylic acid group, per mol of the halogen-substituted isobutylcyclohexanone as the starting material.

In this route, the carboxylic acid salt and the starting material halogen-substituted isobutylcyclohexanone are added in the above-mentioned carboxylic acid and heated at a temperature of from 100° to 250° C., preferably from 150° to 200° C., whereby the desired BFL forms. The reaction time is usually from a few hours to several ten hours. After the completion of the reaction, the desired BFL may be obtained from the reaction solution by a usual separation and purification means such as extraction or distillation. In this route, a part of BFL is assumed to be present in the form of a carboxylic acid ester in the reaction solution. Accordingly, it is preferred to conduct hydrolytic treatment of the ester by adding a mineral acid and water to the reaction solution prior to the separation of BFL.

Route 3: The halogen-substituted isobutylcyclohexanone is heated in the presence of a dehydrohalogenation agent to effect dehydrohalogenation and cyclization to form a 2,2-dimethyl-2,3-dihydro-7-halobenzofuran of the formula VIII, at least one metal selected from the group consisting of lithium, sodium and magnesium is reacted thereto and the resulting metal compound is oxidized and then hydrolyzed to obtain BFL.

As the dehydrohalogenation agent, there may be used a tertiary amine such as pyridine, picoline, collidine, quinoline, triethylamine or dimethylaniline, a quaternary ammonium salt such as tetraethylammonium chloride or benzyl trimethyl ammonium chloride, an organic phosphine such as triphenyl phosphine or tributyl phosphine, an organic phosphine oxide such as triphenylphosphine oxide or tributylphosphine oxide, or an amide such as dimethylformamide, N-methylacetanilide or N,N-dimethyl benzoic acid amide. Preferred is an organic phosphine such as triphenylphosphine or a heterocyclic tertiary amine such as pyridine. The dehydrohalogenation agent is usually used in an amount of from 0.001 to 100 mols, preferably from 0.1 to 10 mols, per mol of the halogen-substituted isobutylcyclohexanone as the starting material.

The heating temperature is usually from 50° to 250° C., preferably from 150° to 200° C., and the reaction time is usually from 0.1 to 10 hours. As the reaction solvent, there may be used xylene, trimethyl benzene, tetramethylbenzene, propyl benzene, butyl benzene, ethyleneglycol or methyl cellosolve. However, without using such a solvent, the reaction readily proceeds while generating a hydrogen halide. After the completion of the reaction, the reaction solution is washed with water to remove the hydrogen halide and then distilled to obtain a 2,2-dimethyl-2,3-dihydro-7-halo-benzofuran of the formula VII.

The reaction of the 2,2-dimethyl-2,3-dihydro-7-halobenzofuran of the formula VIII with a metal may be conducted by firstly dissolving the 7-halobenzofuran of the formula VIII in a proper solvent, for instance, an ether such as tetrahydrofuran, dioxane, ethylene glycol, dimethyl ether or a hydrocarbon such as hexane, benzene or toluene, and then adding a metal in an amount of from 0.1 to 2.5 mols, preferably from 0.2 to 1.2 mols, per mol of the 7-halobenzofuran of the formula VIII and stirring the mixture.

As the metal, there may be mentioned lithium, sodium or magnesium. However lithium or magnesium is preferred. Further, magnesium is preferably in the form of fine powder obtained by reducing a magnesium halide with potassium metal.

The reaction temperature is usually from −20° to 200° C., preferably from 0° to 150° C., and the reaction time is the time required for the added metal to dissolve and is usually from 0.1 to 10 hours.

Further, in the case where magnesium is used as the metal, a reaction accelerator selected from the group consisting of a halogen, an alkyl halide and an alkali metal halide may be used. Specifically, iodine, bromine, sodium iodide, sodium bromide, 1,2-dibromoethane, ethylbromide and methyliodide may be mentioned. Such a reaction accelerator is added in an amount of from 0.001 to 0.1 mol, preferably from 0.005 to 0.05 mol, per mol of the 2,2-dimethyl-2,3-dihydro-7-halobenzofuran.

The reaction of the 7- halobenzofuran with the metal is assumed to proceed as follows:

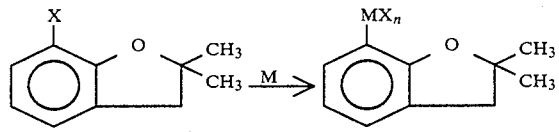

where X is a halogen atom, M is a metal and n is 1 or 0.

The solution obtained by the reaction of the 7-halobenzofuran with the metal is then oxidized by an oxidizing agent. As the oxidizing agent, oxygen or a peroxide such as benzoyl peroxide or t-butylperoxide is usually employed. However, it is economically advantageous to use air.

This oxidation reaction is conducted usually at a temperature of from −20° to 150° C., preferably from 0° to 50° C., and the reaction time is usually from 0.1 to 10 hours, preferably from 0.5 to 5 hours.

This oxidation reaction is preferably carried out in the presence of an alkyl magnesium halide such as isopropyl magnesium chloride, isopropyl magnesium bromide or t-butyl magnesium chloride. A cycloalkyl magnesium halide such as cyclohexyl magnesium bromide and an allyl magnesium halide such as benzyl magnesium bromide may also be used. The amount of the alkyl magnesium halide is usually from 0.5 to 2 mols, preferably from 0.8 to 1.2 mols, per mol of the 2,2-dimethyl-2,3-dihydro-7-halobenzofuran as the starting material.

This oxidation reaction is assumed to proceed as follows:

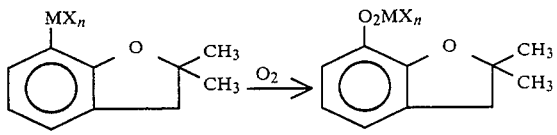

After the completion of the oxidation reaction, the reaction product is hydrolyzed to obtain the desired BFL. This hydrolysis can readily be carried out by adding water or a combination of water and a mineral acid to the reaction system of the oxidation reaction and stirring the mixture at room temperature. It is preferred to use the mineral acid. It is possible to carry out the hydrolysis in an aqueous alkaline solution, but in this case, it will eventually be necessary to neutralize the solution.

From this hydrolytic reaction solution, the desired BFL may be obtained by an usual separation and purification means such as extraction or distillation.

The halogen substituted isobutyl cyclohexanone is useful as an intermediate for the preparation of Carbofuran. Further, it is a precursor for hydroxybenzene and it is also expected to be useful as an intermediate for the preparation of various medicines, agricultural chemicals or perfumes.

Now, the present invention will be described in further detail with reference to Examples. It should be understood that the present invention is by no means restricted by these Examples.

EXAMPLE 1

(i) Preparation of 2-isobutylidene cyclohexanone

While stirring a mixture of 52.5 g (0.536 mol) of cyclohexanone and 13.5 g (0.188 mol) of isobutylaldehyde, a solution prepared by dissolving 2.2 g of sodium hydroxide in 50 ml of methanol is dropwise added to the mixture at a temperature of from room temperature to 40° C., and reacted at room temperature for 2 hours. After the reaction, 20 ml of benzene was added, and the reaction mixture was washed three times with 100 ml of water. From the organic layer, benzene and unreacted cyclohexanone were recovered by distillation, and the distillation was continued, whereby 2-isobutylidene cyclohexanone was obtained in the yield of 37% (based on the isobutylaldehyde) under reduced pressure of 6 mmHg at a temperature of from 95° to 105° C.

(ii) Preparation of 2,2-dichloro-6-chloro-6-(1-chloroisobutyl)cyclohexanone

Into 3.8 g of crude tetrachloroisobutyl cyclohexanone containing 2,2-dichloro-6-chloro-6-(1-chloroisobutyl)cyclohexanone and 2.5 g of its isomer, 0.05 g of pyridine was added and while blowing chlorine in at a rate of from 0.2 to 0.25 mol/hr, the temperature was raised to 90° C. While supplying chlorine at the same rate, a mixture of 30.0 g of 2-isobutylidene cyclohexanone having a purity of 82% and 1.2 ml of pyridine was added to the reaction system at a rate of 7 ml/hr in 3.5 hours. During this period, stirring was continued while maintaining the reaction temperature at a level of from 90° to 100° C. After the completion of the addition of 2-isobutylidene cyclohexanone, chlorine was further supplied at the above-mentioned rate at 90° C. for 0.5 hour.

After cooling the reaction solution, it was washed three times with 20 ml of water and then distilled, whereby 40.0 g (82% yield based on 2-isobutylidene cyclohexanone) of a fraction of 135° to 141° C. was obtained under reduced pressure of 3 mmHg. This fraction had a diffractive index of $n_D^{22}$ 1.5220. This fraction was identified to be 2,2-dichloro-6-chloro-6-(1-chloroisobutyl)cyclohexanone by the following spectra and data.

Elemental analysis

|  | C | H | Cl |
|---|---|---|---|
| Calculated value (%) | 41.1 | 4.79 | 48.6 |
| Analysis value (%) | 41.3 | 4.83 | 48.2 |

IR Spectrum: C=O 1740 cm$^{-1}$.

NMR Spectrum (standard substance: tetramethyl silane, solvent; carbon tetrachloride, 100 megacycle)

| 1.04 ppm (double of doublet) | hydrogen of the methyl group of the isobutyl group | 6.1 H |
|---|---|---|
| 1.7 to 3.2 ppm (multiplet) | hydrogen of the methylene and at the 2-position of isobutyl | 7.3 H |
| 4.5 to 4.7 ppm (multiplet) | hydrogen at the 1-postion of isobutyl | 1.0 H |

Mass Spectrum:
290 (M+).

On the other hand, the reaction solution was analyzed by gas chromatography, whereby a peak other than the peak of the desired compound was observed. The gas chro-mass spectrum of this substance was measured, whereby the main peak was 290. When reacted with an excess amount of pyridine, this substance gave 2-chloro-6-isobutylyl phenol. Thus, this substance was found to be an isomer of 2,2-dichloro-6-chloro-6-(1-chloroisobutyl)cyclohexanone. The yield of this substance was 18% based on the isobutylidene cyclohexanone.

EXAMPLES 2 TO 4

2,2-Dichloro-6-chloro-6-(1-chloroisobutyl)cyclohexanone was prepared in the same manner as in Example 1 except that the catalyst, the solvent, the reaction time and the reaction temperature were varried as shown in Table 1. The results thereby obtained are shown in Table 1.

TABLE 1

| | Solvent | Catalyst Kind | Percent by weight (based on isobutylidene cyclohexanone) | Reaction Condition Temp. (°C.) | Time (hr) | Yield* (%) |
|---|---|---|---|---|---|---|
| Exp. 2 | 2,2,6,6-tetracloro cyclohexanone | Triphenyl phosphine | 2 | 100 | 0.5 | 90 |
| Exp. 3 | 2,2,6,6-tetracloro cyclohexanone | Pyridine | 4 | 100 | 0.5 | 89 |
| Exp. 4 | 2,2,6,6-tetracloro cyclohexanone | Collidine | 5 | 100 | 0.5 | 87 |

*The yield represents the yield of the mixture of 2,2-dichloro-6-chloro-6-(1-chloroisobutyl)cyclohexanone and its isomer.

EXAMPLE 5

Into a mixture comprising 1.0 g of 2-isobutylidene cyclohexanone and 0.1 g of 2,2,6,6-tetrachloro cyclohexanone, an equimolar amount, based on 2-isobutylidene cyclohexanone, of chlorine was blown in at 90° C. in 30 minutes. To this reaction solution, 0.02 g of triphenylphosphine was added and further 3 mols of chlorine per mol of 2-isobutylidene cyclohexanone was blown in at 90° C. in 30 minutes, and thereafter the reaction was continued at 90° C. for 30 minutes. From the analytical results of the product, it was found that a mixture of 2,2-dichloro-6-chloro-6-(1-chloroisobutyl)-cyclohexanone and its isomer was obtained in 42% yield based on 2-isobutylidene cyclohexanone.

EXAMPLE 6

Preparation of 2,2-dimethyl-2,3-dihydro-7-hydroxybenzofuran by the dihydrohalogenation, hydrolysis and cyclization of 2,2-dichloro-6-chloro-6-(1-chloroisobutyl)cyclohexanone A mixture of 5.0 g of 2,2-dichloro-6-chloro-6-(1-chloroisobutyl)cyclohexanone and 50 ml of pyridine was reacted for 4 hours under reflux of the pyridine. The reaction solution was cooled and extracted with 200 ml of water and 50 ml of benzene, whereupon 2.84 g (91% yield based on 2,2-dichloro-6-chloro-6-(1-chloroisobutyl)cyclohexanone)) of 2-isobutenyl-6-chlorophenol was obtained. One gram of 2-isobutenyl-6-chlorophenol was dissolved in 8.46 g of an aqueous solution containing 5.44% by weight of sodium hydroxide and reacted together with 24 mg of cuprous chloride in a SUS autoclave at 180° C. for 3.5 hours, whereupon 1,2-dihydroxy-3-isobutenylbenzene was obtained in 70% yield.

The reaction solution was neutralized with hydrochloric acid and extracted with benzene. After distilling the benzene off, 30 mg of paratoluene sulfonic acid was added to the residue and the mixture was heated and stirred at 120° C. for 1 hour. The reaction solution was dissovled in 5 ml of benzene and extracted with 5 ml of an aqueous solution containing 10% by weight of sodium hydroxide. The aqueous layer was made acidic with hydrochloric acid and then extracted with benzene, whereupon 0.6 g (67% yield based on 2-isobutenyl-6-chlorophenol) of 2,2-dimethyl-2,3-dihydro-7-hydroxybenzofuran was obtained.

EXAMPLE 7

0.32 g of 2,2-dichloro-6-chloro-6-(chloroisobutyl)cyclohexanone, 0.40 g of sodium acetate, 0.003 g of cuprous chloride and 2 ml of acetic acid were sealed in a glass ampul and stirred at 180° C. for 12 hours. After cooling, the ampul was opened and the reaction solution was filtered. The filtrate was distilled under reduced pressure to remove acetic acid. To the residue of the distillation, 2 ml of water and 0.1 ml of concentrated hydrochloric acid were added and the mixture was refluxed for 1 hour. To this reaction mixture, 2 ml of benzene was added and stirred. Then, the benzene layer was analyzed by gas chromatography, whereby it was found that the yield of 2,2-dimethyl-2,3-dihydro-7-hydroxybenzofuran was 13%.

EXAMPLE 8

(i) Preparation of 2,2-dimethyl-2,3-dihydro-7-chlorobenzofuran

To 1.00 g of a distilled solution obtained by the reaction of 2-isobutylidene cyclohexanone with pyridine, 0.1 molar equivalent of triphenylphosphine was added, and the mixture was heated to 200° C. in a nitrogen atmosphere under stirring, whereby hydrogen chloride was vigorously generated. After conducting the reaction at 200° C. for 1 hour, the reaction mixture was cooled, and 5 ml of benzene and 5 ml of water was added for washing with water. The benzene layer was distilled, whereby 0.42 g of the fraction of 65° to 70° C./4 mmHg (the yield of the mixture was 67% based on 2,2-dichloro-6-chloro-(1-chloroisobutyl)cyclohexanone) was obtained. This fraction was identified to be 2,2-dimethyl-2,3-dihydro-7-chlorobenzofuran by the following spectra.

NMR (standard substance: trimethylsilane, solvent; carbontetrachloride, 100 megacycle)

| 1.43 ppm | Singlet: hydrogen of methyl on the dihydrofuran ring | 6.0 H |
| --- | --- | --- |
| 3.0 ppm | Singlet: hydrogen of methylene on the dihydrofuran ring | 2.0 H |
| 6.5 to 7.1 ppm | Multiplet: hydrogen on the benzene ring | 3.1 H |

Mass spectrum: 182 (M+).

(ii) Preparation of a metal compound

Into a solution prepared by dissolving 0.36 g of 2,2-dimethyl-2,3-dihydro-7-chlorobenzofuran in 0.5 ml of tetrahydrofuran, 0.048 g of magnesium metal, 0.003 ml of 1,2-dibromoethane and 0.003 g of potassium iodide were added, and the mixture was heated and stirred under a nitrogen atmosphere and in a bath at a temperature of 100° C. for 2 hours. Then, 0.5 ml of tetrahydrofuran was further added, and the mixture was heated and stirred in a bath at 100° C. for 1 hour. This operation was repeated three times, whereupon magnesium metal was almost completely dissolved.

(iii) Oxidation and hydrolysis

To the reaction solution, 2 ml of tetrahydrofuran, 2.2 ml of t-butylchloride and 0.038 g of magnesium metal were added and the mixture was stirred in a bath at 0° C. for 2 hours. The reaction solution was cooled to room temperature and vigorously stirred for 5 hours under an oxygen atmosphere at room temperature. Then, 2 ml of benzene, 2 ml of water and 0.5 ml of concentrated hydrochloric acid were added to the reaction solution, and the mixture was stirred at room temperature for 1 hour. After separating out the aqueous layer, the organic layer was analyzed by gas chromatography, whereby it was confirmed that 2,2-dimethyl-2,3-dihydro-7-hydroxybenzofuran was formed (28% yield).

I claim:

1. A 2,2-dihalo-6-halo-6-(1-haloisobutyl)cyclohexanone represented by the formula

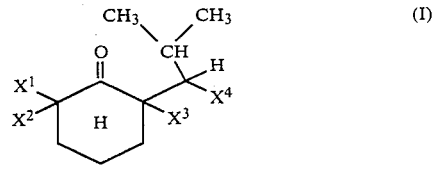

where each of $X^1$, $X^2$, $X^3$ and $X^4$ is a halogen atom.

2. The compound according to claim 1 wherein each of $X^1$, $X^2$, $X^3$ and $X^4$ in formula I is a chlorine atom.

3. A process for preparing a 2,2-dihalo-6-halo-6-(1-haloisobutyl)cyclohexanone represented by the formula:

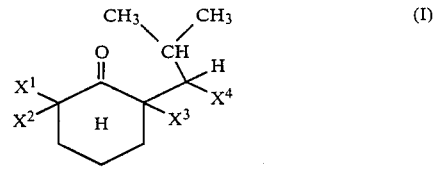

wherein each of $X^1$, $X^2$, $X^3$ and $X^4$ is a halogen, which comprises: reacting 2-isobutylidene cyclohexanone with from 3 to 6 moles of a halogen per mole of 2-isobutylidene cyclohexanone in the presence of a catalyst selected from the group consisting of a teritary amine, an organic phosphine and an organic phosphine oxide.

4. The process according to claim 3 wherein each of $X^1$, $X^2$, $X^3$ and $X^4$ in formula I is a chlorine atom.

5. The process according to claim 3 wherein the reaction product is utilized as a solvent.

* * * * *